United States Patent [19]

Chu et al.

[11] Patent Number: 6,004,563

[45] Date of Patent: *Dec. 21, 1999

[54] FELINE VACCINE COMPOSITIONS AND METHOD FOR PREVENTING CHLAMYDIA INFECTIONS OR DISEASES USING THE SAME

[75] Inventors: Hsien-Jue Chu; Lloyd Chavez; William M. Acree, all of Fort Dodge, Iowa; Lucille W. S. Chang, Hercules, Calif.

[73] Assignee: American Home Products Corporation, Madison, N.J.

[ * ] Notice: This patent is subject to a terminal disclaimer.

[21] Appl. No.: 08/467,775

[22] Filed: Jun. 6, 1995

Related U.S. Application Data

[63] Continuation of application No. 08/065,741, May 20, 1993, abandoned, which is a continuation of application No. 07/610,229, Nov. 7, 1990, Pat. No. 5,242,686.

[51] Int. Cl.$^6$ .................................................. A61K 39/118
[52] U.S. Cl. .................................... 424/263.1; 424/203.1; 424/234.1
[58] Field of Search .............................. 424/263.1, 184.1, 424/203.1, 234.1; 530/412; 435/245

[56] References Cited

U.S. PATENT DOCUMENTS

| | | |
|---|---|---|
| 2,324,646 | 7/1943 | Rake . |
| 2,355,676 | 8/1944 | Rake . |
| 2,415,234 | 2/1947 | Bunney et al. . |
| 2,417,777 | 3/1947 | Nigg . |
| 3,465,077 | 9/1969 | Baker . |
| 3,577,525 | 5/1971 | Baker . |
| 3,674,864 | 7/1972 | Angelucci . |
| 3,927,209 | 12/1975 | Straub . |
| 4,039,656 | 8/1977 | Straub . |
| 4,039,657 | 8/1977 | McAleer et al. . |
| 4,049,794 | 9/1977 | Straub . |
| 4,118,649 | 10/1978 | Caldwell et al. . |
| 4,132,775 | 1/1979 | Volenec et al. . |
| 4,188,375 | 2/1980 | Straub . |
| 4,267,170 | 5/1981 | Seawell . |
| 4,271,146 | 6/1981 | Seawell . |
| 4,328,208 | 5/1982 | Kurbanov et al. . |
| 4,386,065 | 5/1983 | Waldhalm . |
| 4,474,756 | 10/1984 | Mitsuhashi et al. . |
| 4,567,042 | 1/1986 | Acree et al. . |
| 5,142,027 | 8/1992 | Domen et al. . |
| 5,194,595 | 3/1993 | Wathen et al. . |
| 5,202,430 | 4/1993 | Brian et al. . |
| 5,242,686 | 9/1993 | Chu et al. . |

FOREIGN PATENT DOCUMENTS

| | | |
|---|---|---|
| 254937 | 2/1987 | Czechoslovakia . |
| 0253912 | 7/1986 | European Pat. Off. . |
| 216385 | 3/1984 | Germany . |
| 88/02262 | 4/1988 | WIPO . |

OTHER PUBLICATIONS

Plotkin, S.A. et al. (ed.) "Vaccines", published by WB Saunders Company (Philadelphia), see Chapetr 29 by Ellis, R.W., p. 571, 1988.

Kolar, J.R. et al., *Clinical Evaluation of a Commercial Feline Pneumonitis Vaccine, Feline Practice,* Jan. 1977, pp. 47–50.

Mitzel, J.R. et al., *Vaccination Against Feline Pneumonitis, Am. J. Vet. Res.,* vol. 38, Sep., 1977, pp. 1361–1363.

Wills, Josephine M. et al., *Effect of Vaccination on Feline Chlamydia psittaci Infection,* Infection and Immunity, vol. 55, No. 11, Nov. 1987, pp. 2653–2657.

Kolar, J.R., PhD et al., *Duration of Immunity in Cats Inoculated with a Commercial Feline Pneumonitis Vaccine, Veterinary Medicine/Small Animal Clinician,* Aug. 1981, pp. 1171–1173.

Shewen, P.E. et al., *A Comparison of the Efficacy of a Live and Four Inactivated Vaccine Preparations for the Protection of Cats Against Experimental Challenge with Chlamydia psittaci, Can. J. Comp. Med.,* 44:244–291 (Jul. 1980).

Cello, Robert M., *Microbiological and Immunologic Aspects of Feline Pneumonitis, J. Am. Vet. Med. Ass.,* vol. 158, No. 6, pp. 932–943.

*Canine and Feline Immunization Guidelines,* Council Report, *JAVMA,* vol. 195, No. 3, Aug. 1, 1989, pp. 314–317.

Ott, R.L., *Comments on Feline Pneumonitis, J.V.A.M.A.,* vol. 158, No. 6, Mar. 15, 1971, pp. 939–941.

Becerra, V.M. et al., *Studies on the Response of Ewes to Live Chlamydia Adapted to Chicken Embryos or Tissue Culture, Can. J. comp. Med.,* vol. 40—Jan., 1976, pp. 46–52.

McKercher, D.G. et al., *Vaccination of Cattle Against Epizootic Bovine Abortion, Cornell Vterinarian,* vol. 59, pp. 211–226 (1969).

Baker, James A., *Comments on Feline Pneumonitis, J.A.V.M.A.,* vol. 158, No. 6, Mar. 15, 1971, pp. 941–943.

Hamre, Dorothy et al., *Feline Pneumonitis (Baker), A New Member of the Lymphogranuloma–Psittacosis Group of Agents, Journal of Infectious Disease,* vol. 74, pp. 206–211 (1944).

(List continued on next page.)

*Primary Examiner*—Patricia A. Duffy
*Attorney, Agent, or Firm*—Darby & Darby

[57] ABSTRACT

This invention provides a feline vaccine composition comprising an immunogenically active component having inactivated mammalian chlamydial cells or antigens derived there-from, in combination with an effective amount of an immunogenically suitable adjuvant; and a veterinary pharmaceutically acceptable carrier or diluent. The vaccine composition is useful to prevent chlamydia, e.g. *C. psittaci*, infections or diseases in felines, and may also be combined with other vaccine compositions or therapy. A process for producing *C. psittaci* suitable for use in the production of safe and effective chlamydia vaccines, and a method for preventing chlamydia infections or diseases in felines, are also provided.

24 Claims, 5 Drawing Sheets

OTHER PUBLICATIONS

Hamre, Dorothy et al., *Feline Pneumonitis (Baker), A New Member of the Lymphogranuloma–Psittacosis Group of Agents, Journal of Infectious Disease,* vol. 74 (1944), pp. 206–211.

Hamre, Dorothy et al., *Morphological and Other Characteristics of The Agent of Feline Pneumonitis Grown in The Allantoic Cavity of The Chick Embryo, J. Exptl. Medicine,* vol. 86 (1977), pp. 1–6.

Baker, James A., *A Virus Causing Pneumonia in Cats and Producing Elementary Bodies,Journal Exptl. Medicine,* vol. 79, Pp. 158–172 (1944).

Stirling, P. et al., *Interference with Transformation of Chlamydiae from Reproductive to Infective Body Forms by Deprivation of Cysteine, FEMS Microbiology Letters,* 19 (1983), pp. 133–136.

Christensen, Penelope, J., *A New Approach to the Description of Colony Color of Cytophagas and Their Allies, Can. J. Microbiol.,* vol. 20, 1974, pp. 937–942.

*Steadman's Medical Dictionary,* 24th Ed. "Chlamydia", p. 263.

Provost, P.J. et al., *Attempted Immunization Against Trachoma Infection in Baboons, American Journal of Veterinary Research,* vol. 33, pp. 599–605, Mar. 1972.

Collier, L.H. et al., *Dissemination and Immunogenicity of Live Tric Agent in Baboons after Parenteral Injection, American Journal of Ophthalmonology,* vol. 63, pp. 1589–1602 (1967).

Becerra, V.M., et al., *Tissue Culture Adaptation and Pathogenic Properties of an Ovine Chlamydial Abortion Strain, Zbl. Vet. Med. B.* 21, pp. 290–301 (1974).

McEwen, A.D., et al., *Enzootic Abortion in Ewes: Prolonged Immunity Following the Injection of Adjuvant Vaccine, The Veterinary Record,* pp. 686–690, Oct. 6, 1956.

Becerra, V.M., et al., *Studies on Conditions of Interaction between Chlamydiae and Cultured Animal Cells, Zbl. Bakt. I.Abt. Orig.,* 214, Pp. 250–258 (1970).

McEwen, A.D., et al., *Enzootic Abortion in Ewes: Immunisation and Infection Experiments, The Veterinary Record,* vol. 63, pp. 197–201 (1951).

McEwen, A.D., et al., *Enzzotic Abortion in Ewes: Comparative Studies of Different Vaccines, The Veterinary Record,* vol. 66, pp. 393–397 (1954).

Mitscherlich, Von E., et al., *Die Bekampfung des Virusabortes der Schafe, Berl. Munch. Tierarztl. Wsch.,* 78. Jg., Heft 5, (1965).

Yilmasz, Von S., et al., *Erfahrungen bei der Bekampfung des enzootischen Abortes der Schafe mit einer Lebendvakzine asu dem abgeschwachten Chlamydia ovis–Stamm P, Berl. Munch. Tierarztl. Wschr.,* 86 Jg., Heft 19, (1973).

Schoop, G., et al., *Erfahrungen mit einer Lebendvakzinezur Bekampfung des Miyagawanellenabortesder Schafe\*), Zbl. Vet. Med.,* Reihe, B., Bd. 15, Heft 2 (1967).

Neviestic, A., et al., *Aktivna Imunizachija U Profilaksi Enzootskog Pobacaja Ovaca, Broj.* 6, pp. 423–427 (1969).

McEwen, A.D., et al., *Enzootic Abortion in Ewes: An Adjuvant Vaccine Prepared from Eggs, The Veterinary Record,* pp. 393–394 (1995).

McEwen, A.D., et al., *Enzootic Abortion in Ewes: The Recovery of the Virus from the Internal Organs of the Aborted Foetus, The Veterinary Record,* pp. 690–691, (1956).

Young, Stuart, et al., *Abortion in Sheep Due to a Virus of the Psittacosis–Lymphogranuloma Group, J.A.V.M.A.,* pp. 374–379 (1958).

Hulet, C.V., *Observations on Lambing Performance of Sheep Vaccinated Against Ovine Viral Abortion, Am. J. Vet. Res.,* vol. 26, pp. 1464–1466 (1965).

Frank, F.W., et al., *Artifically Induced Immunity to Enzootic Abortion in Ewes, Am. J. Vet. Res.,* vol. 29, pp. 144–1447 (1968).

Meinershagen, W.A., *Efficacy of Combined Bacterius for Experimental Immunization of Sheep Against Ovine Vibriosis and Chlamydial Abortion of Ewes, Am. J. Vet. Res.,* vol. 32, pp. 51–57 (1971).

McKercher, D.G., *Feline Pneumonitis: I. Immunization Studies in Kittens, Am. J. Vet. Res.,* pp. 557–561 (1952).

*Variants of Importance in Medical Bacteriology, Bacterial Variation,* Ch. p, pp. 412–416.

Buxton, A., et al., *Rickettsias and Viruses, Animal Microbiology,* vol. 2, pp. 377–388.

Schachter, J., *Psittacosis (Ornithosis, Feline Pneumonitis and Other Infections with Chlamydia Psittaci), Diseases Transmitted from Animals to Man,* Chapter XXII, pp. 369–381.

McKercher, D.G., et al., *Epizootiologic and Immunologic Studies of Epizootic Bovine Abortion, Cornell Vet.,* 56, pp. 433–450 (1966).

Boidin, A.G., et al., *A Pleuropneumonialike Organism and a Virus in Ovine Pneumonia in California,* pp. 410–430.

Edward, A.G., et al., *Production of Colostrum–Deprived Specific Pathogen–Free Calves, Laboratory Animal Care,* vol. 17, pp. 103–109 (1967).

Eugster, A.K., et al., *Pathogenic Events in Intestinal Chlamydial Infections Leading to Polyarthritis in Calves, The Journal of Infectious Diseases,* vol. 123, pp. 41–50 (1971).

Gimenez, D.F., *Staining Rickettsiae in Yolk–Sac Cultures, Stain Technology,* pp. 135–140.

Kawakami, Y., et al., *Studies on the Disease of Cattle Caused by a Psittacosis–Lymphogranulmoa Group VIrus (Miyagawanella), Japan J. Exp. Med.,* vol. 25, pp. 51–63 (1955).

Page, L.A., *Proposal for the Recognition of Two Species in the Genus Chlamydia,* Jones, Rake and Stearns, 1945, *International Journal of Systematic Bacteriology,* vol. 18, pp. 51–66 (1968).

Reed, L.J., et al., *A Simple Method of Estimating Fifty Per Cent Endpoints, The American Journal of Hygiene,* vol. 27, pp. 493–497 (1938).

Smith, P.C., et al., *Pathogenicity of a Strain of Chlamydia Psittaci of Bovine Intestinal Origin for Neonatal Calves, Am. J. Vet. Res.,* vol. 34, pp. 615–618 (1973).

Storz, J., et al., *Intestinal Bacterial Changes in Chlamydia–Induced Primary Enteritis of Newborn Calves, Annals New York Academy of Sciences,* pp. 162–175.

Storz, J., et al., *Detection and Separation of Simultaneous Enterovirus and Intestinal Chlamydia Infection of Calves,* pp. 75–81.

York, C.J., et al., *A New Member of the Psittacosis–Lymphogranuloma Group of Viruses that Causes Infection in Calves, The Journal of Experimental Medicine,* vol. 93, pp. 587–604.

York, C.J., et al., *Miyagawanella Bovis Infection in Calves, Annals New York Academy of Sciences,* pp. 210–214.

Schutte, A.P., *Chlamydiose by Skape en Beeste in Suid-Afrika, J. South African Vet. Assoc.,* 48(4), pp. 261–265.

Valder, Von W.A., et al., *Untersuchungen zur Wirksamkeit der Vakzination gegen den Chlamydienabort des Schafes,* Dtsch. Tierarztl. Wschr., vol. 82, pp. 221–225 (1975).

Zemjanis, R., *Vaccination for Reproduction Efficacy in Cattle,* Journal of the American Veterinary Medical Association, vol. 165, pp. 689–692 (1974).

Mitzel, J.R., et al., *Cross Immunity Among Strains of Chlamydia Psittaci (35176),* P.S.E.B.M., 135(3) (1970), pp. 944–946.

McKercher, D.G., et al., *Vaccination Against Epizootic Bovine (Chlamydia) Abortion,* J.A.V.M.A., vol. 163, pp. 889–891 (1973).

Mitzel, J.R., et al., *Evaluation of Feline Chlamydial Pneumonitis Vaccine in Cats,* ASM Abstracts of the Annual Meeting–1976, p. 72, e 55.

Waldhalm, D.G., et al., *Pathogenicity of Chlamydia Psittaci After Serial Passage in Chicken Embryos,* Theriogeneology, vol. 11, pp. 441–444 (1970).

Sayed, H., et al., *Differences in Physicochemical and Antigenic Properties of Chlamydial Strains,* Can. J. Microbiol., vol. 22, pp. 937–941 (1976).

Storz, J., et al., *Taxonomy of the Chlamydiae: Reasons for Classifying Organisms of the Genus Chlamydia, Family Chlamydiaceae, in a Separate Order, Chlamydiales ord. nov., International Journal of Systematic Bacteriology,* vol. 21, pp. 332–334 (1971).

England, J.J., *Chlamydial Diseases of Domestic Animals, Clinical Sciences Newsletter,* vol. 3, pp. 9–11 (1980).

Stokes, Gerald V., *Cycloheximide–Resistant Glycosylation in L Cells Infected With Chlamydia Psittaci, Chemical Abstracts,* vol. 80, p. 252, 143786 (1974).

Griel, L.C., et al., *Abortion in Cattle Associated with the Feeding of Poultry Litter, J. Infectious Disease,* pp. 226–234 (1969).

McKercher, G., et al, *Experimentally Induced Immunity Chlamydial Abortion of Cattle,J. Infectious Disease,* vol. 128, pp. 231–234 (1973).

Mitsui et al., Science 145:715–716 1964.

FELINE VACCINE COMPOSITIONS AND METHOD FOR PREVENTING CHLAMYDIA INFECTIONS OR DISEASES USING THE SAME

This is a continuation of application Ser. No. 08/065,741, filed May 20, 1993 now abandoned, which is a continuation of application Ser. No. 07/610,229, filed Nov. 7, 1990 now U.S. Pat. No. 5,242,686.

The present invention relates to vaccines for veterinary use. In particular, the invention relates to vaccines comprising a combination of one or more immunologically active components, i.e. inactivated *Chlamydia Psittaci* or antigens derived therefrom, for prevention and treatment of chlamydia diseases in mammals, such as cats. The invention also relates to methods for immunizing and treating such animals with such vaccines.

BACKGROUND OF THE INVENTION

Feline *Chlamydia psittaci* is the etiologic agent for a common conjunctual and respiratory disease of cats known as feline pneumonitis (FPn) (Baker, J. A. (1942) *Science* 96:475–476). This highly contagious disease is characterized by sneezing and coughing and is accompanied by mucopurulent ocular and nasal discharges (Baker, J. A. (1944) *J. Exp. Med.* 79:159–172). All age groups of cats are susceptible and although mortality is not great, infected kittens and older animals may become severely debilitated. Furthermore, because of its extreme communicability, FPn constitutes a major problem in pet hospitals, clinics and catteries, etc.

Feline Chlamydial infection, like chlamydial infections in other species which are clinically manifested by ocular disease, is not restricted to the conjunctival mucosa. For example, it has been shown that chlamydia inoculation into pathogen-free kittens produced conjunctivitis and rhinitis as well as positive identification of chlamydia in the superficial gastric mucosa (Gaillard, E. T. et al. (1984) *Am. J. Vet. Res.* 45:2314–2321). In another study, *C. psittaci* was recovered from a female cat, with persistent genital tract infection, resulting from ocular rather than direct genital infection (Darougar, S. M. et al. (1977) pages 186–198 in D. Hobson and K. K. Holmes (Ed.) *Nongonococcal Urethritis and Related Infections,* American Society for Microbiology, Washington, D.C.). Persistent genital tract infection by *C. psittaci* is believed to be a cause of reproductive failure in catteries, however the mechanism of such failure is unclear. The mode of extraocular transmission and the contribution of extraocular infection to the persistence and pathology of feline chlamydial disease is unknown.

Vaccination studies with modified-live compositions has produced conflicting results. Modified live chlamydial vaccines in general have shown variable efficacy ranging from no protection (Cello, R. M. J., *Am. Vet. Med. Assoc.* 158:932–938, 1971) to partial protection (Shewen, P. E., et al., *Can. J. Comp. Med.* 44:244–251, 1980) to almost complete protection (McKercher, D. G., *Am. J. Vet. Res.* 13:557–561, 1952; Mitzel, J. R., and A. Strating, A. J. Vet. Res. 38:1381–1363, 1977; Kolar, J. R. and T. A. Rude, *Feline Practice* 7:47–50, 1977 and *Vet. Med. S.A. Clin.* 76:1171–1173, 1981; Wills, J. M. et al., *Infec. Immun.* 55:2653–2657, 1987). However, in studies demonstrating vaccine efficacy, chlamydia was isolated in conjunctival swabs from vaccinated cats 24 days post challenge (Mitzel and Strating, 1977), 31 days post challenge (Kohler and Rude, 1977), and as late as 68 days post challenge (Wills et al., 1987) with sporadic isolations occurring between 3 and 8 months post challenge (Wills, J. M. Ph.D. thesis, University of Bristol, England, 1986). In addition, Wills et al. (1978) have demonstrated that excretion of chlamydia from vaccinated cats was actually prolonged when compared to the controls. No difference could be demonstrated between the vaccinates and controls in the amount of chlamydial shedding from the eyes or the transmission of the organism to the gastrointestinal and genital tracts.

Similar studies with inactivated chlamydial preparations produced mixed results. In one feline study where the efficacy of a killed preparation was evaluated, irradiated and crystal violet treated, purified yolk sac suspensions were described and used (McKercher, D. G., *Am. J. Vet. Res.* 13: 557–561, 1952). The induced protection was comparable to that of modified-live vaccines similarly purified, but was inferior to a modified-live crude yolk sac preparation. On the hand, comparative challenge studies conducted with four inactivated vaccine preparations and a commercial modified-live vaccine demonstrated that the inactivated preparations conferred virtually no protection against chlamydial infection in felines (Shewen, P. E. et al., *Can. J. Comp. Med.* 44: 244–251, 1980).

The egg yolk sac-propagated FPn used to prepare the known modified-live and inactivated preparations is also known to contain a large amount of a toxin (Hamre, D. et al., *J. Infect. Dis.* 74:206–211 (1944). Release of this toxin, lipopolysaccharide, or another unidentified antigen(s) onto the eye during FPn infection may contribute significantly to the pathogenesis of the ocular disease caused by this organism.

Because of the documented inability of prior modified live preparations to reduce shedding, and the probability that modified-live vaccinated infected animals could shed both the vaccine and field strains, with the concomitant risk of recombination, reactivation, and communication of disease to surrounding uninfected animals, the need exists for the development of safe, efficacious inactivated *C. psittaci* vaccines. Moreover, prior inactivated preparations have been unsuccessful or markedly inferior to modified-live preparations.

OBJECT OF THE INVENTION

It is an object of the present invention to provide an inactivated feline chlamydia vaccine composition having high antigen load in combination with a potent adjuvant which will elicit corresponding antisera when administered systemically to a subject feline.

It is another object of the present invention to provide a process for producing *C. psittaci* suitable for use in the production of safe, effective chlamydia vaccines.

It is a further object of the present invention to provide a method for preventing chlamydia infection in felines by immunizing these animals with an efficacious inactivated vaccine composition.

These and other objects will become more apparent in light of the detailed description which follows.

SUMMARY OF THE INVENTION

The present inventors have discovered that an immunogenically active component can be made and usefully incorporated into a vaccine composition for preventing chlamydia infections in mammals, i.e. felines. The immunogenically active component has inactivated, e.g., chemically inactivated, chlamydial (chlamydia) cells or antigens derived therefrom, such as outer membrane extracted antigens. The immunogenically active component is combined with an effective amount of an adjuvant, and a veterinary pharmaceutically acceptable carrier or diluent therefor.

The present invention also provides a purification process whereby toxic immunogenic substances in egg yolk sac cultures containing C. psittaci are removed when said cultures are further subcultured in mammalian cells, i.e. dog kidney cells.

DETAILED DESCRIPTION OF THE INVENTION

Figure 1:
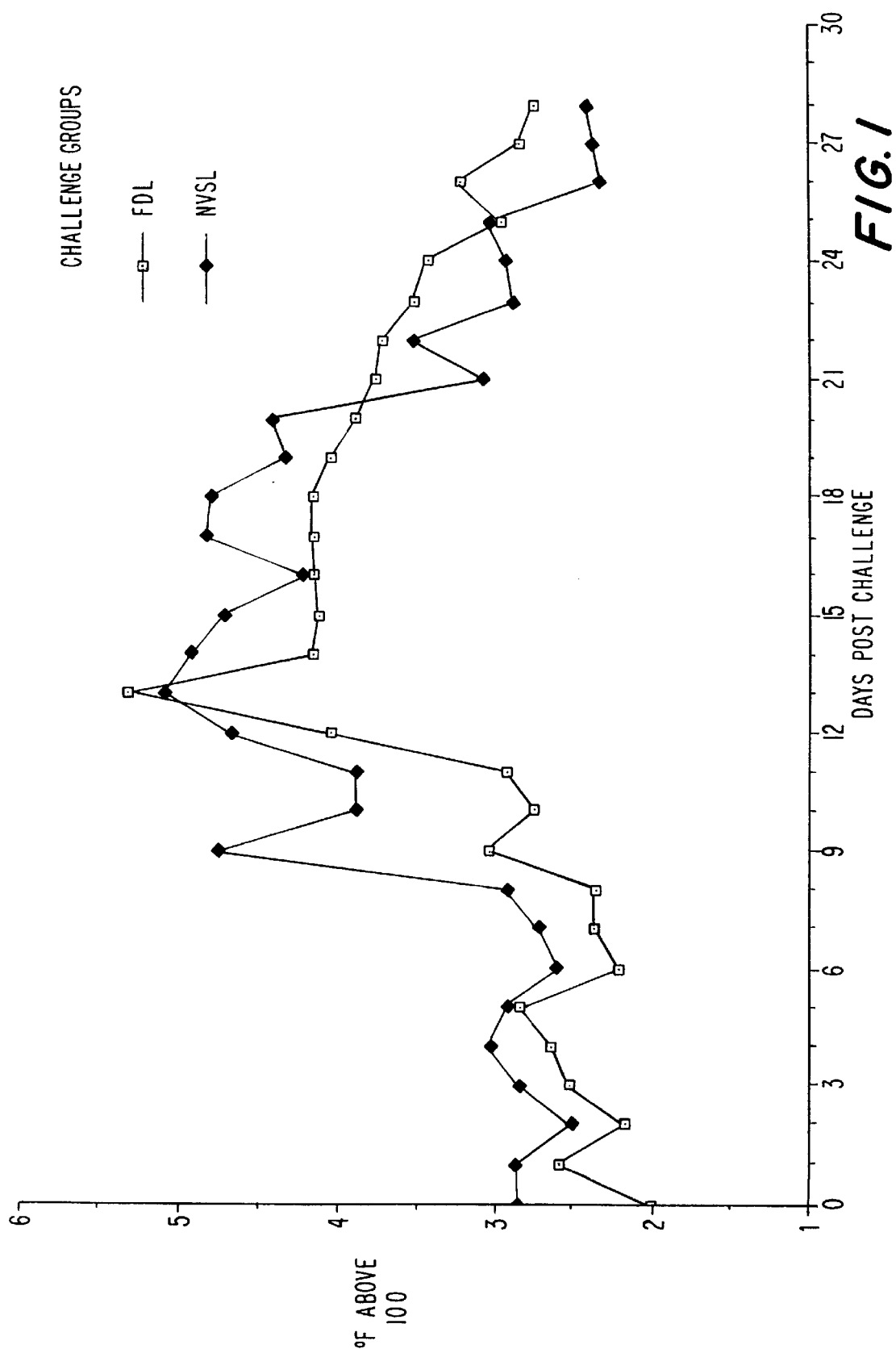
FIG. 1 is a plot of daily mean temperature response versus days post challenge of two groups of non-vaccinated felines challenged with two low egg passage chlamydia preparations.

All literature references, patents and patent applications cited in this specification are hereby incorporated by reference in their entirety.

The present invention provides a vaccine composition comprising an immunogenically active component having inactivated *Chlamydia psittaci* or antigens derived therefrom in combination with an effective amount of an adjuvant; and a veterinary pharmaceutically acceptable carrier or diluent therefor.

As used herein, the term "immunogenically active" component refers to the ability of the component described herein to stimulate an immune response, i.e., to cause the production of antibodies and/or a cell-mediated response when introduced into a subject (mammal, e.g. feline). More specifically, the term "immunogenically active" component refers to the ability of this component to stimulate secretory antibody and/or cell-mediated response production in local mucosal regions, e.g. the surface of the upper respiratory tract and/or conjunctiva, and the cervico-vaginal cavity, when administered systemically as a vaccine composition according to the present invention.

*Chlamydia psittaci* organisms used to make the immunogenically active components of the present vaccine composition can be obtained from university or research institutes, e.g. National Veterinary Services Laboratory (NVSL) (Ames, Iowa) or can be isolated from the fluids or tissues of infected mammals. Such sources include, for example, blood, vaginal, cervical, ocular, pneumonic, gastral, nasal fluids, discharges, secretions and scrapings. In particular, the viral pathogens can be isolated from ocular and nasal secretions. Isolated *Chlamydia psittaci* can best be maintained in egg yolk cultures.

According to the invention, a chlamydia isolate obtained from NVSL (Lot No. 87-16-1) was first propagated in an egg yolk culture. Seed chlamydia from this isolate was diluted in Dulbecco's phosphate buffered saline (PBS), pH 7.0, and inoculated into the egg yolk sac of six or seven day old embryonated SPF eggs at the concentration of 100 to 1000 ELD$_{50}$ per egg. The diluted seed was provided in a volume of 0.1 ml. The eggs were wiped with a 2% tincture of iodine mixture or similar chemical disinfectant. A small hole was drilled in the middle of the air sac and the inoculum inserted into the yolk sac with a 22 gauge needle. The hole was sealed with glue. The inoculated embryonated eggs were incubated for five to ten days in 37° C. ±1° C. incubator. The eggs showed normal development and growth until day 6 or 7 post inoculation, when the vascular system starts to break down, indicating embryo death from chlamydia. Contamination would be observed by the death of the embryo during the first three days after inoculation. All eggs dying up to day 3 and other eggs demonstrating signs of contamination were discarded. Elapsed time between inoculation and harvest was five to ten days for the embryonated eggs. The eggs were kept at 2–9° C. for two to four hours before harvest.

A usual intermediate seed harvest consisted of approximately 200 infected embryonated eggs. The egg yolk and chorioallantoic membranes from up to 100 eggs were combined into sterile pooling containers for each lot. Up to a 50% volume of PBS was added to the containers and the infected membranes were blended in a mechanical blender. The infected mixture was centrifuged at 1000 rpm for 15 minutes and the PBS middle layer containing chlamydial elementary bodies was drawn off. A stock of 40% sorbitol was added (to a final concentration of 10%) as a stabilizer. Other stabilizers, such as sucrose, NZ Amine, and SGGK may also be used.

The harvested material was aliquoted into 100 ml amounts and frozen at −50° C. until used as seed for at least one subsequent passage in a suitable cell line. For example, chlamydia can be subcultured in cell lines derived from sources such as feline, canine, avian, equine, ovine, caprine, bovine, swine, mouse and human, said cell lines comprising fibroblasts or epithelial, synovium, lung, spleen, amnion, stomach, kidney, cornea, liver, testicles, laryngeal tumor and HeLa cells. Dog kidney cells are preferred as a cell line for subculturing yolk-sac propagated chlamydia.

A dog kidney cell line [MDCK(NBL-2)] was purchased from the American Type Culture Collection (ATCC No. CCL-34, passage no. 55), subcultured, and stored at −70° C. or lower before use. The dog kidney cell growth medium consisted of Eagle's minimum essential media. (MEM) to which the following may be added: not more than 10% bovine serum or serum substitutes, not more than 0.5% lactalbumin hydrolysate, not more than 0.5% bovine serum albumin, Neomycin at a concentration of 30 mcg/mL, and not more than 2.5 mcg/mL Amphotericin B. Kidney cell monolayers can be grown in 850 or 1750 cm$^2$ disposable roller bottles, 1700 or 3500 cm$^2$ disposable pleated roller bottles or in bioreactors capable of holding 10 to 2000 L volumes.

Just prior to tissue culture inoculation, seed chlamydia was diluted in a chlamydia inoculation medium which consisted of Eagle's MEM with the following additions: not more than 0.5% lactalbumin hydrolysate, not more than 10 mcg/mL polybrene, Neomycin at a concentration of 30 meg/mL and not more than 2.5 mcg/mL Amphotericin B. Growth medium was discarded when cell sheets were approximately 100% confluent. The diluted inoculum was added aseptically to production containers at a MOI of 1:10 to 1:1000 for tissue culture. The inoculum was adsorbed for up to 24 hours at 37° C. At the end of the adsorption period, the inoculum was discarded, the monolayer was rinsed and chlamydia propagation medium was added.

Chlamydia propagation medium consisted of Eagle's MEM with the following additions: not more than 0.5% bovine serum albumin, and/or 0.5% bovine serum and/or 0.5% lactalbumin hydrolysate, not more than 0.0158 M sucrose, not more than 20 mM Hepes, Neomycin at a concentration of 30 mcg/mL, and not more than 2.5 mcg/mL Amphotericin B. Chlamydia propagation media was added to production flasks as follows: up to 500 mL for 850 cm$^2$ disposable roller bottles, up to 1000 mL for 1750 cm$^2$ disposable roller bottles and 1700 cm$^2$ disposable pleated roller bottles, and up to 2000 mL for 3500 cm$^2$ disposable pleated roller bottles. Chlamydia propagation media could also be added to bioreactor vessels, if used, as follows: up to 10 L for 10 L vessels, up to 30 L for 30 L vessels, up to 100 L for 100 L vessels, up to 400 L for 400 L vessels and up to 2000 L for 2000 L vessels.

After inoculation, the cells do not exhibit cytopathology. Contamination would be observed by clouding of the medium, and any unsatisfactory or questionable cultures are eliminated. Tissue cultures were incubated for 7 to 21 days at 33–37° C. Tissue culture vessels may be examined for indications of adequate chlamydial growth by making a cell smear from the infected monolayer of one of the tissue culture vessels and checking the smear by indirect immunofluorescence assay (IFA) for characteristic inclusion bodies. Vessels were also inspected for gross indications of pH changes and contamination.

Elapsed time between inoculation and harvest was 7–21 days for the tissue culture passages. Only cultures considered free of bacteria and fungi by macroscopic examinations were harvested.

For a single harvest, fluids were harvested aseptically by removing the contents of the culture bottles into sterile pooling containers. To remove the infected cell monolayers, MEM containing 1:20,000 thimerosal at a volume of up to one-vessel tenth the chlamydial propagation media was added to each vessel. The vessel was rolled at 37° C. until the infected monolayer started to come off (up to 4 hours). The media containing the infected cells was combined with the supernatants and enough thimerosal was added to the total volume to bring the thimerosal concentrations to 1:20,000. The thimerosal serves the dual purpose of removing the infected monolayer from the bottle and inactivating the live chlamydia. Alternatively, the infected monolayer of cells may be removed by freezing the bottles at −20° C. or below for 4 to 24 hours. Samples may be taken from the pooled supernatants plus infected cells for determination of the Enzyme Linked Immunosorbent Assay (ELISA) antigenic value and for sterility and inactivation tests.

For multiple harvest of infected materials, the cultures may be refed and harvested up to six times by adding chlamydia propagation media to the bottles or bioreactor and incubating for an additional 5 to 14 days for each multiple harvest. The final harvest shall consist of supernatants and infected cells harvested by the above-described procedures. Fluids for vaccine use may consist of supernatant only and/or supernatants plus infected cells.

As one measure of vaccine potency, each individual or pooled lot should have an acceptable ELISA antigen value as measured against a reference vaccine. Inactivated chlamydia may be concentrated and/or pooled with other harvests, such that the averaged antigenic value meets or exceeds the minimum acceptable value.

Inactivated chlamydial fluids may be concentrated up to 20 fold, if necessary, by ultrafiltration, with a molecular weight cutoff of 100,000 daltons, or by differential centrifugation. Concentrates were stored at 2–9° C. until mixed or microfluidizied with adjuvant.

Following their harvest and separation as whole cell isolates, chlamydia may be inactivated by conventional inactivation means. For example, inactivation of whole cell isolates can be achieved by contacting the cells with an inactivating agent. Suitable agents include, without limitation, binary ethylenimine, betapropiolactone, formalin, merthiolate, thimerosal, gluteraldehyde, sodium dodecyl sulfate, triton-100, acetone, ether, phenol, heat (e.g. 56° C. for 5 or more minutes), ultraviolet irradiation in the presence or absence of psoralen, gamma irradiation, or a combination of any of these agents in an aqueous suspension. Preferred as a chemical inactivating agent is thimerosal at a final concentration of 1:20,000 for 3 days.

After inactivation, the inactivated chlamydial (chlamydia) whole cells can be adjusted to an appropriate concentration which meets or exceeds the minimum acceptable ELISA antigen value in combination with an immunogenically stimulating adjuvant. The preinactivation chlamydia titers of such antigen preparations generally range from $10^{5.0}$ to $10^{6.5}$ ELD$_{50}$ per dose. When antigens derived from chlamydial (chlamydia) cells, e.g., *C. psittaci*, are employed, a suitable amount of protein or antigen per dose may be used, for example, 50 to 1,000 ug/dose.

As used herein the term "immunogenically stimulating adjuvant" refers to an agent, compound or the like, which potentiates or stimulates the immune response in a subject animal when administered in combination with the inactivated whole cells. Thus, the immune response, elicited by the inactivated whole cell-adjuvant combination, as measured by antibody and/or cell-mediated response, will generally be greater than that provoked by the inactivated whole cells alone.

The immunogenically stimulating adjuvants augment the immune response provoked by the inactivated chlamydia cells. The inactivated chlamydia cells may or may not elicit a desired immune response, e.g., a local mucosal and/or a strong systemic immunity, when systemically administered alone. An essential feature of the present invention is the combination of the inactivated chlamydia cells and immunogenically stimulating adjuvant, which provide the desired immune response.

Non-limiting examples of the immunogenically stimulating adjuvants used in the practice of the present invention are surfactants, e.g., hexadecylamine, octadecylamine, lysolecithin, dimethyldioctadecyl-ammonium bromide, N,N-dioctadecyl-N'-N-bis (2-hydroxyethylpropane diamine), methoxyhexa-decylgly-cerol and pluronic polyols, saponin, Quil A; polyanions or polycations, e.g., pyran, diethylaminoethyl (DEAE) dextran, dextran sulfate, polybrene, poly IC (polynucleotide complex of polyinosinic-polycytidylic acid) polyacrylic acid, carbopol, aluminum hydroxide, aluminum phosphate; peptides, e.g., muramyl dipeptide, dimethylglycine, tuftsin; oil emulsions, immunomodulators, e.g., interleukin-1, interleukin-2; interferon(s); or combinations of any of the foregoing adjuvant agents.

A number of acrylic acid polymers and copolymers of acrylic acid and methacrylic acid and styrene have adjuvant activity. Polyvinyl Chemical Industries (Wilmington, Mass.) provide such polymers under the tradename NEOCRYLO®. NEOCRYL A640, an aqueous acrylic copolymer having pH 7.5, viscosity 100 cps (Brookfield 25° C.), a weight per gallon of 8.6 pounds as supplied containing 40% solids by weight, 38% solids by volume and an acid number of 48, is a preferred adjuvant. Specifically, NEOCRYL A640 is an uncoalesced aqueous acrylic copolymer with styrene. More specifically, NEOCRYL A640 is a latex emulsion of a copolymer of styrene with a mixture of acrylic and methacrylic acid. Other useful NEOCRYL products are 520 and 625, and NEOREZ 966.

Ethylene/maleic anhydride copolymer is another preferred adjuvant. Suitable ethylene/maleic anhydride copolymers useful in this invention are the linear ethylene/maleic copolymers such as EMA-31 (as produced by Monsanto Co., St. Louis, Mo.), a copolymer with approximately equal amounts of ethylene and maleic anhydride, having an estimated average molecular weight of about 75,000 to 100,000. These copolymers are water soluble, white, free-flowing powders having the following typical properties: a true density of about 1.54 g/mL, a softening point of about 170° C., a melting point of about 235° C., a decomposition temperature of about 274° C., a bulk density of about 20 lbs/ft$^3$, and a pH (1% solution) of 2.3.

More preferably, two or more adjuvants will be admixed with the harvested inactivated chlamydiosis (chlamydia) cells or antigens derived therefrom. One preferred combination is ethylene/maleic anhydride copolymer, NEOCRYL A640, and MVP. MVP is a mineral oil adjuvant produced by Modern Veterinary Products (Omaha, Nebr.). Also preferred as an immunogenically stimulating adjuvant is a combination of saponin and aluminum phosphate.

It has been discovered that the adjuvants described above will act in effective amounts to immunogenically stimulate the inactivated chlamydia cells or antigens derived therefrom. As used herein, the effective amount of the immunogenically stimulating adjuvant can comprise from about 0.01% to about 50%, preferably from about 1% to about 5% for EMA/Neocryl®/MVP, and preferably from about 0.01% to about 0.3% for saponin/aluminum phosphate.

The vaccine composition of the present invention also comprises a veterinary pharmaceutically acceptable carrier or diluent. A preferred carrier is saline.

As further embodiments of the present invention, the vaccine composition can be administered, for example, by incorporating the active component into liposomes. Liposome technology is well-known in the art having been described by Allison, A. C. and Gregoriades, G., *Liposomes as Immunologic Adjuvants, Nature* 252:252054 (1974) and Dancy, G. F., Yasuda, T., and Kinsky, S. C., *J. Immunol.* 120:1109–13 (1978). In addition, the active component can be conjugated to suitable biological compounds or materials, such as, for example, polysaccharides, peptides, proteins, or a combination of any of the foregoing. Conjugated vaccines are described by Coon, J., and Hunter, R. L., *J. Immunol.* 110:183–90 (1973).

Also as further embodiments of the present invention, the vaccine composition can be administered as sustained release product(s), for example, by incorporating the vaccine components in polymers, e.g. lactide-glycolide copolymer. Microparticles were previously found to possess adjuvant effect for an entrapped antigen following parenteral administration, as described by Sjoholm, I. and Edman, P., *Microspheres and Drug Therapy in Pharmaceutical, Immunological and Medical Aspects* (Editors Davis, S. S., Illum, I., McVie, J. G. and Tomlinson, E.) Elsevier, Amsterdam, 1984, P. 245–262.

It is advantageous to formulate the vaccine composition of this invention in a dosage unit form to facilitate administration and insure uniformity. Thus, in another embodiment, this vaccine composition can be formulated in dosage unit form comprising at least about $2\times10^4$ inactivated chlamydia cells, preferably at least about $1\times10^5$ cells.

In a further embodiment, the vaccine composition can comprise a parenteral injectable form, again to ease its administration to a subject feline.

The present invention provides a method for preventing chlamydia infection in felines comprising administering to a feline an effective amount of the vaccine composition described above.

The routes of administration contemplated by the present invention are parenteral, e.g., subcutaneous, intramuscular, intraperitoneal and intradermal. Preferred routes of administration are subcutaneous and intramuscular.

It has been discovered that the vaccine composition of the present invention is useful to prevent chlamydia infection in felines that need such protection when administered parenterally, e.g., subcutaneously or intramuscularly, in effective amounts. An effective regimen of treatment includes administering the vaccine composition, for example, in dosage unit form as described above, at least about two times, with each administration separated by about two (2) to about four (4) weeks, preferably from about fourteen (14) to about thirty (30) days or so.

It will be understood by the skilled practitioner that the vaccines of the present invention may be combined with other vaccines to produce a combination vaccine effective against more than one pathogen. Examples include a chlamydia vaccine in combination with one or more vaccines for feline leukemia, panleukopenia, calici, rhinotracheitis, feline acquired immunodeficiency disease, rabies, feline infectious peritonitis, toxoplasmosis, and *Borrelia burgdorferi*.

The working examples set forth below are intended to illustrate the invention without limiting its scope.

EXAMPLE 1

Vaccine Preparations

Killed feline *chlamydia psittaci* (FCP) vaccines were formulated to contain thimerosal-inactivated *C. psittaci* in combination with killed feline leukemia (FeLV), panleukopenia (FPV), calici (FCV) and rhinotracheitis (PCT) viruses. The vaccines contained either $AlPO_4$/saponin or EMA/Neocryl/MVP as adjuvants. As shown in Table 1, six formulations were made, and these were compared with a commercial modified-live product.

TABLE 1

| Vaccine | Adjuvant | FCP[a] Ratio | FCP-ELISA |
|---------|----------|--------------|-----------|
| FCP 1A | Saponin/AlPO$_4$ | 1 | 1.00[b] |
| FCP 1B | Saponin/AlPO$_4$ | 1/5 | 0.20 |
| FCP 2A | Saponin/AlPO$_4$ | 1 | 0.81 |
| FCP 2B | Saponin/AlPO$_4$ | 1/5 | 0.11 |
| FCP 3A | EMV/Neocryl ®/MVP | 1 | 1.00[c] |
| FCP 3B | EMV/Neocryl ®/MVP | 1/5 | 0.36 |
| Eclipse ®4 | N.D | d | N.D |

TABLE 1-continued

| Vaccine | Adjuvant | FCP[a] Ratio | FCP-ELISA |
|---------|----------|--------------|-----------|

[a] This ratio represents the amount of the FCP component in the combination vaccine composition comprising FCP, FeLV, FVR, FCV and FPV components.
[b] FCP 1A served as a reference vaccine for the FCP 1B and FCP 2A ELISA potency determinations, with a value of 1.00.
[c] FCP 3A served as a reference vaccine for the FCP 3B ELISA potency determination, with a. value of 1.00.
[d] The Eclipse ®4 modified-live commercial combination vaccine had modified-live chlamydia as the immunogenic component and is commercially available from Solvay Animal Health, Inc. Because the adjuvant system for Eclipse ®4 is unknown, a meaningful relative FCP-ELISA potency value cannot be determined.

EXAMPLE 2

Challenge and Isolation of *C. Psittaci* in Felines

Two challenge preparations were evaluated in young cats in order to produce consistent disease due to infection with *Chlamydia psittaci*.

A. Experimental Animals

Ten animals used for this experiment were specific pathogen free (SPF) cats purchased from Liberty Laboratories (Liberty Corner, N.J.). The cats were screened after receipt of antibodies to *C. psittaci* utilizing an ELISA assay for *C. psittaci* antibodies. The SPF cats were 10 to 12 weeks of age at the time of vaccination and approximately 16 to 18 weeks old at the time of challenge.

B. Experimental Design

Two 1 mL vaccinations of the FCP 1 and FCP 2 vaccines or fractional dose vaccines were administered intramuscularly 21 days apart. Two doses of Solvay's modified-live Eclipse®4 vaccine were given 21 days apart according to the label directions. Animals receiving the modified live vaccine were held in separate facilities both before and after vaccination to prevent any possible spread of the vaccine strain to other cats. All cats were challenged 22 days post second vaccination and were bled at the time of the first and second vaccinations, and then weekly until at 28 days post challenge.

C. Challenge Preparations

The first challenge preparation was a feline pneumonitis isolate (*Chlamydia psittaci*, strain Cello) which represents the 6th egg yolk sac passage of the material described by Dr. Robert Cello (*Am. J. Opth.* 63:1270–1273, 1967). This reagent (Lot #87-16-1, National Veterinary Services Laboratory) is a 20% yolk sac suspension in brain heart infusion broth and was stored at −70° C. until use. This challenge isolate was further passaged once in egg yolk to produce a second challenge preparation (i.e. low egg passage challenge reagent). The challenge evaluation indicated that both materials can adequately infect cats and produce chlamydial disease (FIGS. 1 and 2).

D. Challenge Procedure

Two groups of five 14 week old SPF cats were challenged with either the NVSL feline pneumonitis challenge material or with the low egg passage FCP preparation derived from the NVSL challenge material. The total amount of Chlamydia given to each cat was $10^{5.5}$ $ELD_{50}$ for the NVSL challenge group and $10^{6.375}$ $ELD_{50}$ for the low egg passaged challenge group. The challenge material was nebulized into the eyes and nares of each cat over a period of 2–3 minutes. Rectal temperatures, conjunctival swabs, throat swabs and blood for serum were taken at intervals for 53 days. The animals were observed daily for clinical signs for 28 days.

E. Chlamydia Detection and Post-Challenge Evaluation

1. Chlamydia Detection

For the challenge evaluation, conjunctival smears were made from both eyes of each cat at intervals starting from the day of challenge until the end of the study. Smears were fixed in acetone, stained by direct FA using FITC-conjugated mouse monoclonal antibody directed toward the chlamydial group antigen (Bartels Immunodiagnostic Supplies, Inc.) and examined for the presence of Chlamydia in ocular cells.

2. Post-Challenge Evaluation

All cats in the challenge evaluation were monitored for 24 hours prior to challenge to establish baselines and for 28 days following challenge. Rectal temperatures and gross clinical signs, including but not limited to ocular discharge, nasal discharge, coughing, sneezing, conjunctivitis, anorexia and depression were recorded daily. Conjunctival smears were taken at intervals starting the day of challenge. Cats were bled weekly starting from the day before challenge and at 7, 14, 21, and 28 days post challenge.

The following criteria were measured and recorded:

Temperature Response

Temperature scoring was based on the following scale:

| °F. | Score |
|---|---|
| <103.0 | 0 |
| 103.0–104.9 | 1 |
| 104.0–104.9 | 2 |
| ≧105.0 | 3 |

Gross Clinical Signs

Clinical points were assigned according to the following scale:

| Clinical Sign | | Score |
|---|---|---|
| Ocular discharge | | |
| Clear (Serous) | -mild | 0.5 |
| | -moderate | 1.0 |
| Mucopurulent | -mild | 1.0 |
| | -moderate | 1.5 |
| | -severe | 2.0 |
| Nasal discharge | | |
| Clear (Serous) | -mild | 0.5 |
| | -moderate | 1.0 |
| Mucopurulent | -mild | 1.0 |
| | -severe | 2.0 |
| Sneezing | | 1.0 |
| Coughing | | 1.0 |
| Anorexia | | 1.0 |
| Depression | | 1.0 |
| Dehydration | | 1.0 |
| Dyspnea | | 2.0 |
| Conjunctivitis | -mild | 0.5 |
| | -moderate | 1.0 |
| | -severe | 2.0 |

Statistical analysis of the temperature response data was accomplished using the Student t-test. Clinical sign data was analyzed by the Student t-test and/or the Mann-Whitney Rank Test. These analyses were performed using the software package Statview 512+ from Brain Power, Inc. on an Apple MacIntosh SE computer.

F. Challenge Results

1. Temperature Response in Cats Following Challenge

The daily mean temperature response in both challenge groups is shown in FIG. 1. A consistent elevation in temperature is evident in both groups starting from day 9 in the NVSL challenge group and day 12 in the low egg passage group. Temperatures in both groups remained elevated until 25–26 days post challenge, then returned to normal (<103° F.). The fever response peaked at 13 days following challenge for both groups. The peak of the average fever response was 105° F. for cats receiving the NVSL challenge preparation and 105.3° F. for those receiving the low egg passage preparation. These data indicate that the temperature response for each challenge material paralleled the other except for a lightly slower initial elevation with the low egg passage challenge material.

2. Clinical Sign Scores of Cats Following Challenge

Figure 2:
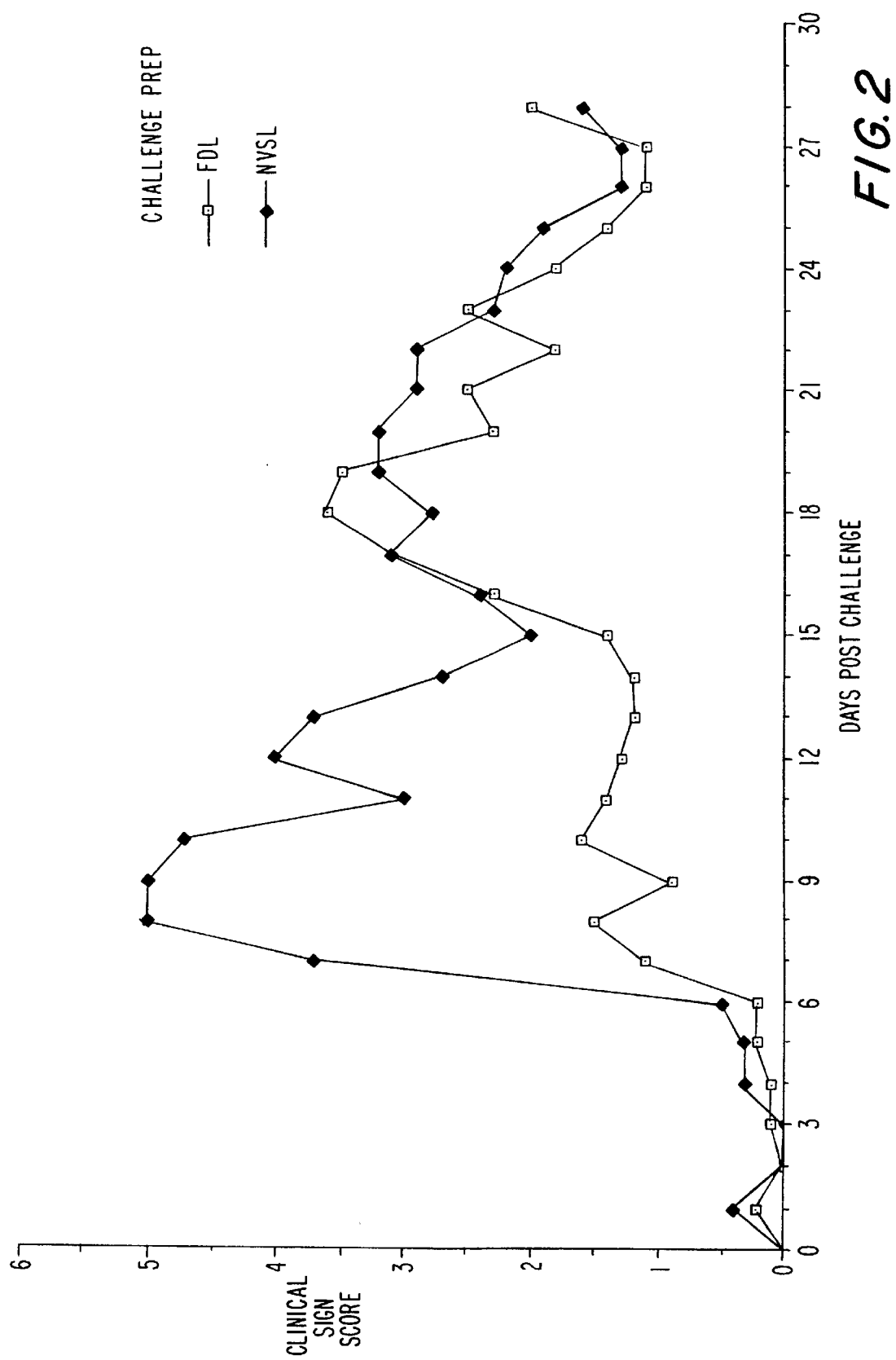
FIG. 2 is a plot of the daily mean clinical sign score versus days post challenge of two groups of non-vaccinated felines challenged as in FIG. 1.

FIG. 2 shows the daily mean clinical score for both challenge groups. Peak clinical signs occurred between days 7 through 13 and days 17 through 22 with both challenge preparations, although the relative level of clinical signs stimulated by the low egg passage preparation in the first peak was lower than by the NVSL challenge preparation.

3. Detection of Chlamydia in Cats Following Challenge

Chlamydia shedding occurred in all cats following challenge. Chlamydia was demonstrated in conjunctival smears starting at 5 days post challenge. Chlamydial isolations were more sporadic in the low egg passage challenge group initially than in the NVSL challenge group. Conjunctival smears in all of the cats were positive on day 25 post challenge.

EXAMPLE 3

Correlation of Immunogenicity and Potency of FCP Vaccines Containing Saponin/AlPO$_4$ as Adjuvants A total of 91 SPF cats, 10 to 12 weeks of age, were utilized in this study. The FCP 1A vaccination group consisted of 21 cats. The FCP 1B and FCP 2A vaccination groups consisted of 20 cats each. The FCP 2B and the Solvay Eclipse®4 vaccination groups included 11 cats each. The non-vaccinated control group consisted of 11 cats. The reagent used to challenge the cats in the immunogenicity trials was a combination of the NVSL challenge preparation and the low egg passage preparation diluted to $10^{5.79}$ FLD$_{50}$ titer per cat. Results indicate a reliable and accurate reproduction of disease from the use of the combined low egg passage preparation and NVSL challenge preparation.

A. Reduction in Fever in Vaccinated Cats As Compared to Controls Following Challenge The temperature response of each animal in the five vaccine and control groups were measured. The peak in the average temperature responses observed are summarized below:

| Vaccine Group | Days. Post-Challenge | Temperature | Mean % Days of Fever |
| --- | --- | --- | --- |
| FCP 1A | 20 | 102.6° F. | 10.6 |
| FCP 1B | 3–20 | 102.5° F. | 9.6 |
| FCP 2A | 10 | 102.8° F. | 17.6 |
| FCP 2B | 9–11 | 102.9° F. | 20.1. |
| Eclipse ®4 | 9 | 102.7° F. | 12.8 |
| Controls | 9 | 104.3 | 34.3 |

These results indicate that the two full strength FCP 1A and FCP 2A vaccines of the invention and the FCP 1B fractional dose vaccine provided significant differences in the temperature response versus the non-vaccinated controls.

Furthermore, there was a significant reduction in the average temperature response varying from five to nine out of the 10 days during which the mean temperature of the controls were equal to or greater than 103.0° F. (indicating fever). These observations are summarized below:

| Vaccine Group | Total Days Showing Significant Difference from Controls | In Vitro Potency Value |
| --- | --- | --- |
| FCP 1A | 9 | 1.0 |
| FCP 1B | 8 | 0.2 |
| FCP 2A | 8 | 0.81 |
| FCP 2B | 4 | 0.11 |
| Eclipse ®4 | 5 | N.D. |

These results indicate a positive correlation between ELISA antigen values (relative to FCP 1A, Example 1) and efficacy in reducing temperature response in the vaccinates following challenge. The FCP 1A, 1B, and FCP 2A vaccines were effective in reducing temperature response, whereas FCP 2B, with an ELISA value of 0.11, was not effective. The FCP 1A, 1B and 2A vaccines were more efficacious than the modified-live vaccine with respect to protection against fever induced by chlamydia challenge.

Figure 3:
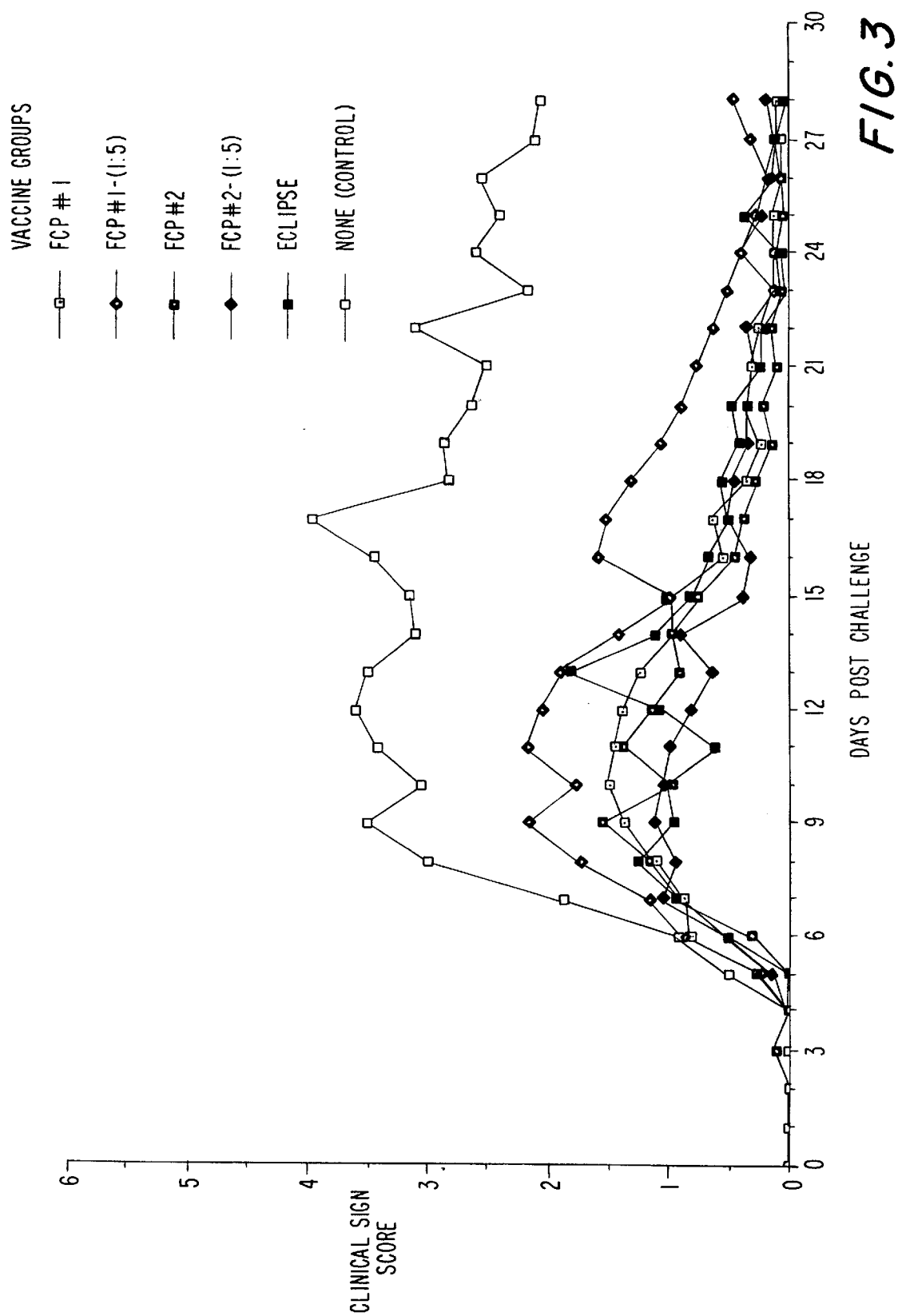
FIG. 3 is a plot of the mean clinical sign score versus days post challenge of five vaccinated and one unvaccinated group of felines challenged with a combination of the two low egg passage chlamydia preparations. The inactivated chlamydia vaccine compositions contained Saponin/AlPO$_4$ adjuvants.

B. Reduction in Clinical Sign Scores in Vaccinated Cats as Compared to Controls Following Challenge The mean clinical sign scores per day per group were calculated according to the actual number of observation days, and are summarized graphically in FIG. 3. There was a significant reduction (p <0.05) in clinical sign scores in each vaccine group, varying from 16 to 24 out of the 24 days during which the non-vaccinated controls had clinical sign scores greater than zero. These observations can be summarized as follows:

| Vaccine Group | Total Days Showing Significant Difference from Controls | In Vitro Potency Value |
| --- | --- | --- |
| FCP 1A | 22 | 1.0 |
| FCP 1B | 23 | 0.2 |
| FCP 2A | 24 | 0.81 |
| FCP 2B | 16 | 0.11 |
| Eclipse ®4 | 22 | NT |

The least protected group was the FCP 2B fractional dose group, although it provided statistically significant reduction in clinical signs versus the control group. In addition, there was no statistical difference in the reduction in clinical signs afforded by the FCP 1A, 1B, 2A and 2B vaccines compared to the modified-live vaccine.

The percent reduction in the mean clinical scores when compared to the mean of the controls was 76.4% for FCP 1A, 80.1% for FCP 1B, 81.1% for FCP 2B, 56.7% for FCP 2B and 79.3% for the modified-live product. Significant differences between each vaccine group and the control group were found. This confirms that the inactivated chlamydial vaccines of the invention are as or more efficacious than the modified-live vaccine.

Figure 4:
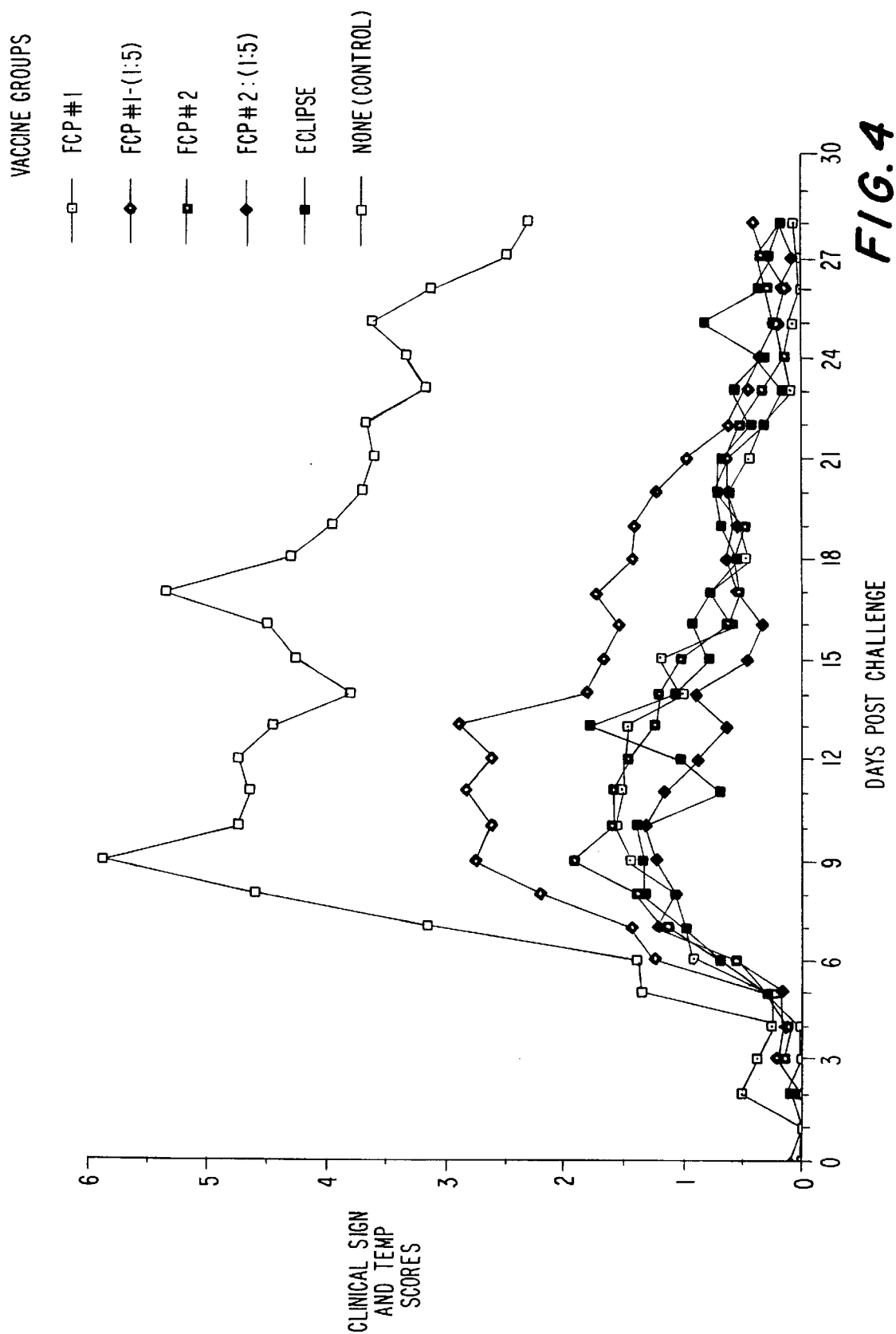
FIG. 4 is a combined plot of the mean clinical sign scores and temperature response versus days post challenge of five vaccinated and one unvaccinated group of felines challenged as in FIG. 3. The inactivated chlamydia vaccine compositions contained Saponin/AlPO$_4$ adjuvants.
Figure 5:
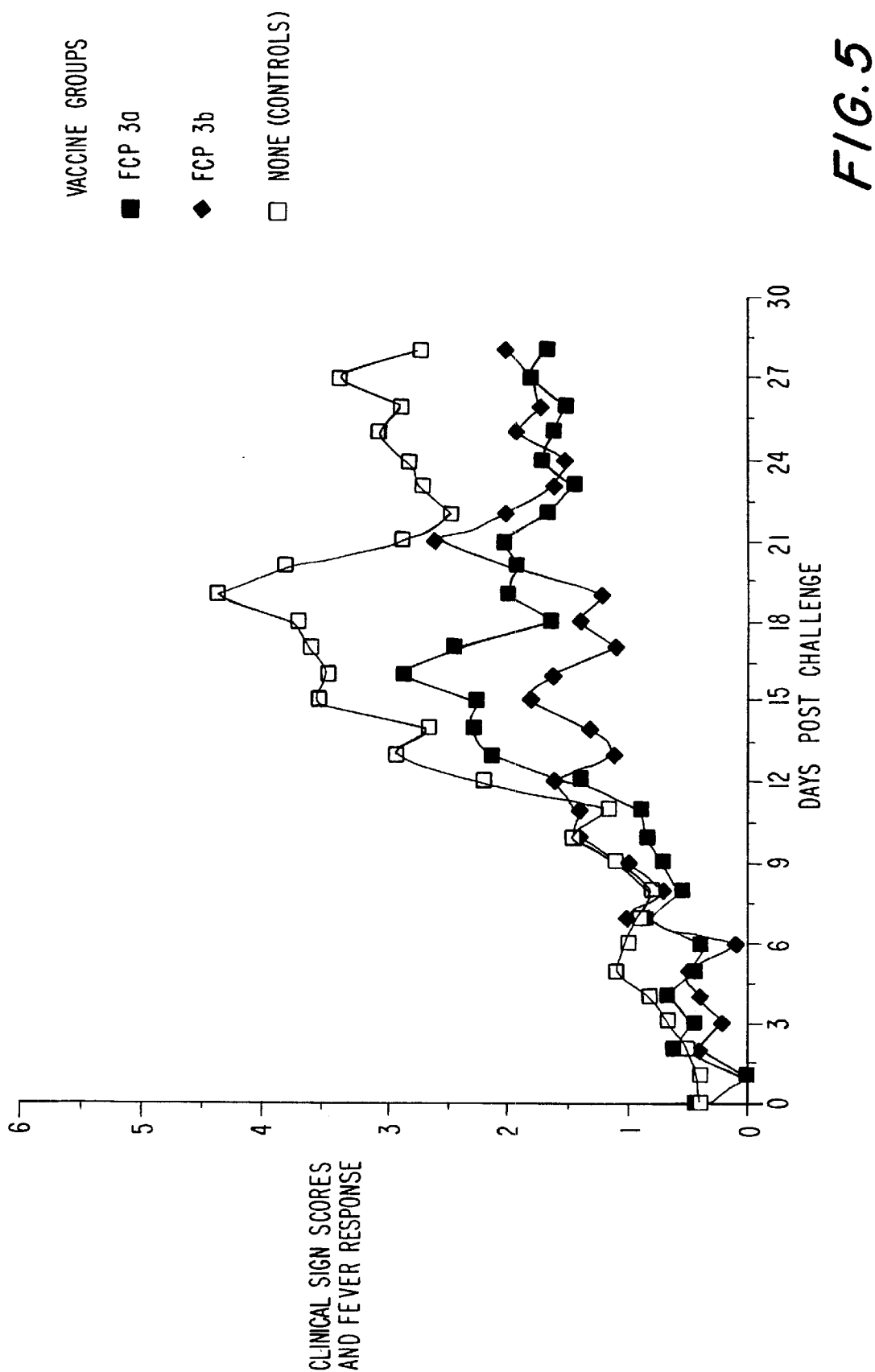
FIG. 5 is a combined plot of the mean clinical sign scores and fever response versus days post challenge of two groups of vaccinated and one unvaccinated group of felines challenged with a low egg passage chlamydia isolate. The inactivated chlamydia vaccine compositions contained EMA/Neocryl®/MVP adjuvants.

C. Reduction in Combined Clinical Sign and Temperature Scores in Vaccinated Cats as Compared to Controls Following Challenge FIG. 4 combines the total clinical sign scores with the scoring from the temperature responses and are in general agreement with the data scored separately. Significant lower combined scores (p<0.05) were found in each vaccine group, varying from 21 to 24 out of the 24 days during which the non-vaccinated controls had clinical sign scores greater than zero. These observations are again summarized below:

| Vaccine Group | Total Days Showing Significant Difference from Controls |
|---|---|
| FCP 1A | 23 |
| FCP 1B | 24 |
| FCP 2A | 24 |
| FCP 2B | 22 |
| Eclipse ®4 | 23 |

The percent reductions in combined scores when compared to the mean of the controls was 77.8% for FCP 1A, 80.5% for FCP 1B, 75.7% for FCP 2A, 53.6% for FCP 2B and 77.1% for Solvay Eclipse®4. As seen for the separate clinical sign score data, significant differences between each vaccine group and the control group were found.

In conclusion, all non-vaccinated control cats developed Chlamydia disease following FCP challenge. The FCP 1A and FCP 2A vaccines and even their corresponding fractional dose vaccines (1B and 2B) were efficacious in protecting vaccinated cats against virulent feline *C. psittaci* challenge. These vaccines and their fractional doses were effective in reducing both fever response and clinical signs in the vaccinates following FCP challenge. Moreover, the inactivated Chlamydia vaccines of the invention were found to be as or more efficacious as the known modified life vaccine.

EXAMPLE 4

Post Challenge Evaluation of Felines Vaccinated With FCP Compositions Containing EMA/Neocryl®/MVP Adjuvant System The efficacy of FCP vaccines containing EMA/Neocryl®/MVP as adjuvants was evaluated in young cats via vaccination and challenge studies. The vaccines were administered intramuscularly or subcutaneously in two doses, 21 days apart. Efficacy of the FCP vaccines was demonstrated by challenging the vaccinated groups and age-match controls with the low egg passage virulent pneumonitis preparation as described below.

A total of 100 healthy, specific pathogen free (SPF) cats were purchased for the FCP vaccine efficacy testing. Ninety-five (95) cats were purchased from Liberty Laboratories (Liberty Crossing, N.J.) and five (5) cats were acquired from Harlan-Spraque Dawley (Indianapolis, Ind.). All test animals were approximately 16 to 20 weeks of age at the time of vaccination and approximately 20 to 25 weeks of age at the time of challenge. These animals were housed in isolation facilities throughout the entire study.

A total of 35 animals were divided into two vaccination groups and one non-vaccinated control group. The 20 cats in the first vaccination group, receiving 1 mL of the full dose of the FCP 3A vaccine (Example 1), were further subdivided into two groups with 10 cats receiving the vaccine subcutaneously and 10 cats receiving the vaccine intramuscularly. A second dose of the vaccine was given 21 days later. Each of the five cats in the second vaccination group received 1 mL of the ⅕th fractional dose FCP 3B vaccine intramuscularly. A second dose of vaccine was given 21 days later. The remaining 10 cats served as non-vaccinated controls.

Twenty one (21) days following the second vaccination, all test cats were challenged with the aforementioned virulent feline pneumonitis preparation. The challenge material was prepared as the first egg yolk passage material from a stock provided by NVSL. The material was aliquoted and stored at 100° C. until use. At the time of challenge, this material was thawed and diluted 1:5 with PBS, to contain $10^{5.375}$ $ELD_{50}$. The Chlamydia was nebulized into the eyes and nares of the cats over a period of two to three minutes. Rectal temperatures and clinical signs were taken daily for 28 days. Conjunctival swabs and blood for serum were taken at weekly intervals.

The following criteria were measured and recorded according to the scoring system described below:

| Fever/Clinical Sign | | Score |
|---|---|---|
| Fever response | | |
| <103.0° C. | | 0 |
| 103.0–103.9° C. | | 1.0 |
| 104.0–104.9° C. | | 2.0 |
| ≧105.0° C. | | 3.0 |
| Ocular discharge | | |
| Clear (serous) | - mild | 0.5 |
| | - moderate | 1.0 |
| Mucopurulent | - mild | 1.0 |
| | - moderate | 1.5 |
| | - severe | 2.0 |
| Nasal discharge | | |
| Clear (serous) | - mild | 0.5 |
| | - moderate | 1.0 |
| Mucopurulent | - mild | 1.0 |
| | - moderate | 1.5 |
| | - severe | 2.0 |
| Sneezing | | 1.0 |
| Coughing | | 1.0 |
| Anorexia | | 1.0 |
| Depression | | 1.0 |
| Dehydration | | 1.0 |
| Dyspnea | | 2.0 |
| Death | | 5.0 |
| Conjunctivitis | - mild | 0.5 |
| | - moderate | 1.0 |
| | - severe | 2.0 |

Analysis of the post-challenge fever and gross clinical signs (i.e. combined fever/clinical sign score) was accomplished by the Mann-Whitney Rank Test. All analyses were performed using the software package Statview 512+ from Brain Power, Inc. on an Apple Macintosh II or SE computer.

The FCP 3A and 3B vaccines demonstrated satisfactory efficacy against the Chlamydia challenge. FIG. 5 shows the mean fever response and clinical sign scores of vaccinated and control cats following FCP challenge.

As expected, the virulent FCP challenge produced a significantly ($p<0.05$) higher fever response and chlamydial clinical signs in the non-vaccinated controls, as compared to the vaccinates (FIG. 5). Following an incubation period of approximately 7±3 days, the virulent FCP-induced fever and clinical signs became increasingly apparent in the control animals and peaked at day 19 post challenge with a combined fever and clinical sign score of 4.35 per animal. Throughout the 28 day post-challenge observation period, the average daily fever/clinical sign score for the controls was 2.19 per animal (FIG. 5).

Comparatively, the degree of the post-challenge fever/clinical sign score for the vaccinates was much milder than that of the controls (FIG. 5). The average daily fever/clinical sign score for the FCP 3A vaccine group and the FCP 3B vaccine group were 1.34 and 1.23 per animal, respectively, as demonstrated in FIG. 5. In addition, during the period when chlamydial disease was overt in the control group (i.e. day 12 through day 28 post challenge), the fever/clinical sign score of either vaccine group was consistently less than that of the control group. Statistically, there is a significant difference ($p<0.05$) when the average daily fever/clinical sign score of either vaccine group was compared to that of the controls. Furthermore, when the daily fever/clinical sign scores of the individual cats receiving the FCP 3A vaccine were compared to those of the ten control cats, a significant difference ($p<0.05$) was observed on days 15, 18, 19, 20, 23, 24, 25, 26, 27 and 28 following challenge. Both the intramuscular route and the subcutaneous route of administering the FCP 3A vaccine were found effective.

Similarly, when the daily fever/clinical sign scores of the FCP 3B vaccine group were compared with those of the controls, a significant difference ($p<0.05$) was obtained on days 6, 13, 16, 17, 18, 19, 20, 23, 24, 26 and 27 following challenge.

In conclusion, these results demonstrate the efficacy of the FCP fraction in the FCP 3A vaccine and its 1:5 fractional dose FCP 3B in protecting vaccinated cats against virulent FCP challenge.

What is claimed is:

1. A vaccine composition against feline *Chlamydia psittaci* infections comprising an immunogenically active component consisting of inactivated feline *Chlamydia psittaci* in a pre-inactivation titer of at least $10^{5.0}$ $ELD_{50}$ per dose, an adjuvant, and a veterinary pharmaceutically acceptable carrier or diluent therefor, wherein said vaccine composition is purified of toxic immunogenic egg yolk sac substances, said vaccine composition prepared by the process comprising:

a) culturing the feline *Chlamydia psittaci* in egg yolk sac;

b) subculturing said egg yolk sac culture containing the feline *Chlamydia psittaci* in a suitable cell line to remove toxic immunogenic substances present in the egg yolk sac culture;

c) harvesting the feline *Chlamydia psittaci* from the contents of the subculture, said contents selected from the group consisting of infected cell line cells, subculture supernatant and a combination thereof;

d) inactivating the feline *Chlamydia psittaci* with inactivating agents; and e) mixing the inactivated feline *Chlamydia psittaci* with the adjuvant and physiologically acceptable carrier or diluent.

2. A vaccine composition of claim 1, wherein said feline *Chlamydia psittaci* are isolated from feline specimens selected from the group consisting of vaginal, cervical, nasal, ocular, pneumonic, gastral fluids, secretions, discharges or scrapings, or a conbinaton of any of the foregoing.

3. A vaccine composition of claim 1, wherein the inactivating agents are selected from the group consisting of binary ethylenimine, beta-propriolactone, formalin, merthiolate consisting of thimerosal and sodium ethylmorcurithio-salicylate, thimerosal, glutaraldehyde, sodium dodecyl sulfate, an alkylaryl polyether alcohol surfactant, and combinations thereof.

4. A vaccine composition of claim 3, wherein said inactivating agent is thimerosal.

5. The vaccine of claim 1, wherein said suitable cell line comprises dog kidney cells.

6. A vaccine composition of claim 1, wherein said adjuvant is selected from the group consisting of surfactants, polyanions, polycations, peptides, tuftsin, mineral oil emulsions, immunomodulators, ethylene/maleic anhydride copolymer, copolymer of styrene with a mixture of acrylic acid and methylacrylic acid and combinations of any of the foregoing.

7. A vaccine composition of claim 6, wherein said adjuvant is one of ethylene/maleic anhydride copolymer, copolymer of styrene with a mixture of acrylic acid and methylacrylic acid, mineral oil emulsion or a combination of any of the foregoing.

8. A vaccine composition of claim 1, wherein said adjuvant is one of saponin and aluminum phosphate or a combination thereof.

9. A vaccine composition of claim 1, wherein said adjuvant comprises from 0.01 to 50% w/v or v/v.

10. A vaccine composition of claim 1, wherein said veterinary pharmaceutically acceptable carrier or diluent comprises saline or Eagle's minimum essential media.

11. A vaccine composition of claim 1, wherein said immunogenically active componet is incorporated into liposomes.

12. A vaccine composition of claim 1, wherein said immunogenically active component is incoporated into sustained release polymer(s).

13. A vaccine composition of claim 1, wherein said immunogenically active component is conjugated to a biological compound selected from a group consisting of polysaccharides, peptides, proteins, or a combination of any of the foregoing.

14. A vaccine composition of claim 1, in a dosage unit form comprising at least $2\times10^4$ inactivated feline *Chlamydia psittaci.*

15. A vaccine composition of claim 1, in parenteral injectable form.

16. A multi-vaccine composition comprising the vaccine composition of claim 1, and at least one vaccine composition directed against a pathogen selected from the group consisting of feline leukemia, panleukopenia, calici, rhinotracheitis, feline acquired immunodeficiency disease, rabies, feline infectious peritonitis, toxoplasmosis, and *Borrelia burgdorferi*, and combinations of any of the foregoing.

17. The vaccine of claim 1, wherein said subculturing comprises one passage in a suitable cell line.

18. The vaccine of claim 1, wherein the cell line subculture is harvested up to six times comprising the steps of:

a) adding new chlamydia propagation media to the cell line subculture following the first harvest;

b) incubating the cell line subculture;

c) harvesting the feline *Chlamydia psittaci* from the contents of the subculture, said contents selected from the group consisting of infected cell line cells, subculture supernatant and a combination thereof; and d) repeating steps a–c up to five times.

19. A method of preventing feline *Chlamydia psittaci* infection in felines comprising administering to a feline in need of such prevention an effective amount of the vaccine composition of claim 1.

20. A method of claim 19, wherein the vaccine composition is parenterally administered.

21. A method of claim 20, wherein said parenteral administration is carried out subcutaneously.

22. A method of claim 20, wherein said parenteral administration is carried out intramuscularly.

23. A method according to claim 19, wherein said vaccine composition is administered at least two times, each administration separated by about 14 to about 30 days.

24. A vaccine composition comprising an immunogenically active component consisting of inactivated feline *Chlamydia psittaci* in a pre-inactivation titer of at least $10^{5.0}$ $ELD_{50}$ per dose, an adjuvant and a veterinary pharmaceutically acceptable carrier or diluent therefor, wherein said vaccine composition is purified of toxic immunogenic yolk sac substances.

* * * * *